United States Patent [19]

Egli et al.

[11] 3,992,113
[45] Nov. 16, 1976

[54] PHOTOMETER CIRCUITRY FOR THE DIGITAL INDICATION OF THE LIGHT ABSORPTION OF A TEST SAMPLE

[76] Inventors: Bruno Egli, Promenadenstrasse 21, Rorschach; Manser Niklaus, Pestalozzistrasse 2, Goldach, both of Switzerland

[22] Filed: Apr. 21, 1975

[21] Appl. No.: 570,134

Related U.S. Application Data

[60] Continuation-in-part of Ser. No. 525,618, Nov. 20, 1974, abandoned, which is a division of Ser. No. 353,965, April 24, 1973, Pat. No. 3,879,135.

[52] U.S. Cl. ............................. 356/206; 356/223
[51] Int. Cl.² ..................................... G01N 21/22
[58] Field of Search ............ 356/223, 229, 206, 226

[56] References Cited
UNITED STATES PATENTS

| | | | |
|---|---|---|---|
| 3,528,749 | 9/1970 | Bowker | 356/229 |
| 3,664,744 | 5/1972 | Liston | 356/229 |
| 3,843,265 | 10/1974 | Egli | 356/223 |

*Primary Examiner*—John A. Corbin
*Assistant Examiner*—Conrad Clark
*Attorney, Agent, or Firm*—Andrus, Sceales, Starke & Sawall

[57] ABSTRACT

Photometer circuitry includes a capacitor discharge means for establishing a time period related to the light absorption properties of a test sample. The time period is used, in conjunction with a frequency generator to drive a digital counter to provide a digital indication of light absorption.

7 Claims, 4 Drawing Figures

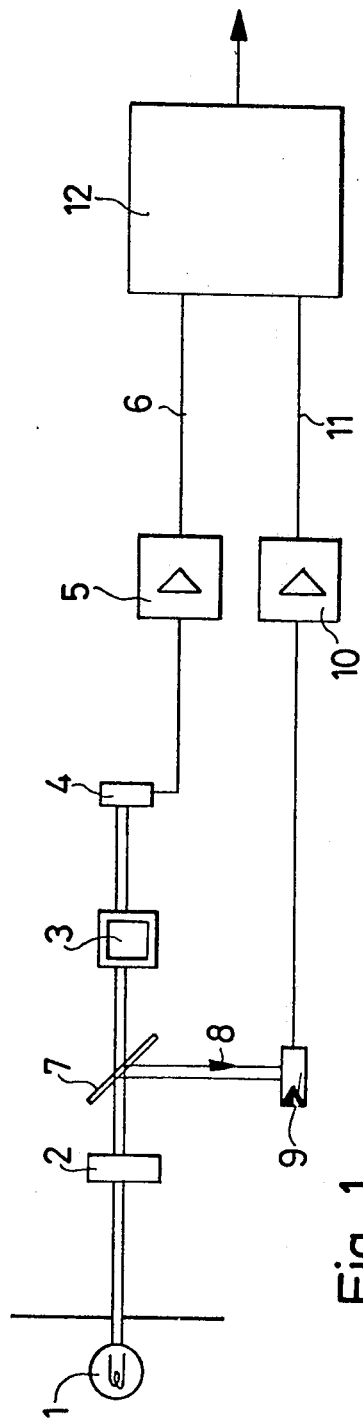
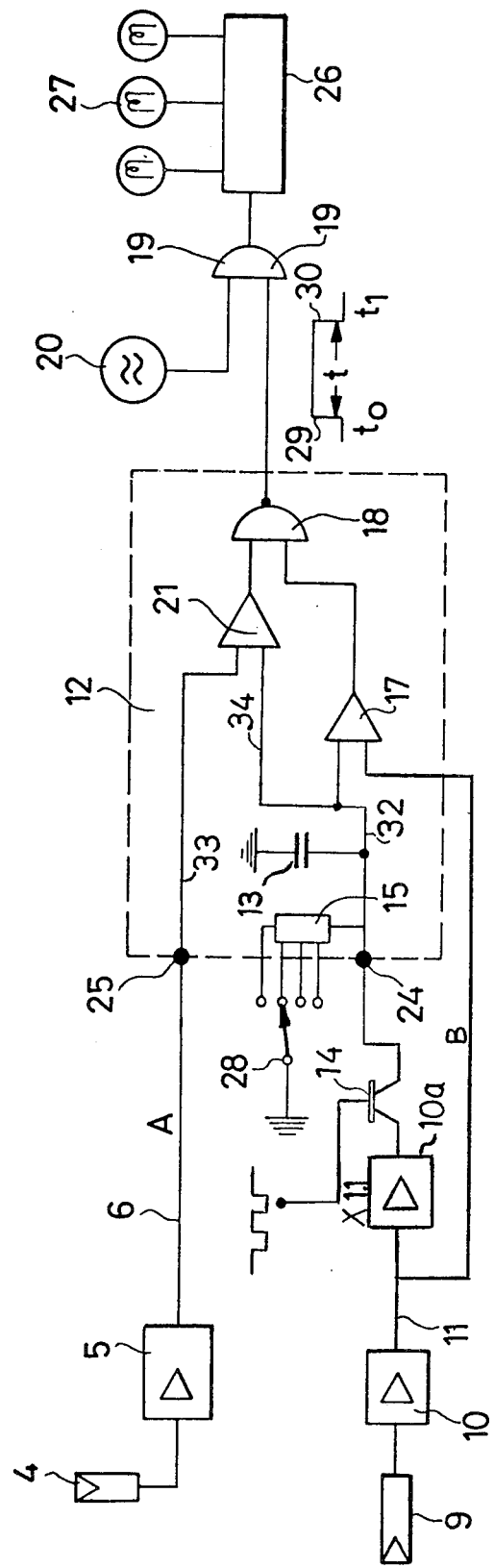
Fig. 1
Fig. 3

$$t_1 - t_0 = t \approx F \cdot \log \frac{B}{A} = E_A \cdot F$$

PHOTOMETER CIRCUITRY FOR THE DIGITAL INDICATION OF THE LIGHT ABSORPTION OF A TEST SAMPLE

CROSS REFERENCE TO RELATED APPLICATION

This application is a continuation-in-part application of copending application, Ser. No. 525,618 filed Nov. 20, 1974 and now abandoned. Application 525,618 is a divisional application of Ser. No. 353,965, filed Apr. 24, 1973 and now U.S. Pat. No. 3,879,135.

BACKGROUND OF THE INVENTION

1. Field of the Invention

The present invention is directed to a photometer for providing a digital indication of the light absorption properties of the test sample.

2. Description of the Prior Art

In known photometers a light beam is passed through a test sample in a glass cuvette or test cell and applied to a photoelectric sensor. The photoelectric sensor provides a voltage in accordance with the light absorbance of the test sample which is used for readout purposes. As the criteria for the light translucent properties of the test sample is the result of the light falling on the photoelectric sensor, the brightness qualities of the light source enter into the test results. With null balance, one may compensate for momentary brightness deviations but balance will be valid only for short times. Accordingly, the resulting comparison is affected in that every alteration of lamp brightness causes a migration of the reading from null. The intensity of the light source also varies rather strongly with stabilizing voltage so that exact measurement is not possible without continuous control and adjustment of the null point.

The purpose of the invention of the herein-described photometer is to provide, with minimal apparatus costs, continuous compensation for brightness variation of the illumination source. The purpose is further to provide, in addition to this brightness variation compensation, a time period which is directly proportional to the test results and which may be used to control a digital indicating or readout device.

To accomplish the foregoing purposes, the present invention provides a photometer for digitally indicating the light absorption properties of a test sample in a cuvette. The basis for the light absorption indication is the discharge time of a capacitor which is determined by the voltage difference between a light intensity responsive voltage produced by the application of a light beam to a comparison cell and a light intensity responsive voltage dependent on the light emerging from the measuring cell cuvette. The former voltage is used to charge the capacitor and the latter voltage terminates the discharge of the capacitor.

As criteria for the light transmission properties of the analyzed sample, the ratio of the quantity of the light applied to the sample to the quantity of light emerging from the sample will thus be employed. For this purpose a comparison light beam will be generated which is proportional to the intensity of the light rays applied to the cuvette. It is preferable in order not to diminish the useful intensity of the light rays which are applied to the analysis sample to divert only a small part of the light quantity in the generation of the comparison ray. By sufficiently high amplification with an amplifier, a signal which corresponds to the light intensity applied to the cuvette may be obtained. A measuring sensor, for example, a photoelectric sensor senses the light transmitted through the analysis sample. Electrically, with the help of the discharge characteristics of a capacitor, the quotient of both the value of the measuring light beam and value of the comparison light beam will be used in obtaining the results. This result is dependent on the quotient of the value of the measuring and comparison light beams. As the result is not dependent on the brightness of the light source not only does extremely good long term stability result but the burning time of the lamp is shorter and heat generation less than with conventional apparatus.

Through the discharge of a capacitor with an exponential discharge curve, the time t is provided as a function of the discharge. As this discharge period is logarithmically proportional to the value of the measuring and comparison light beams, it can be applied to the control of a digital counter. In the indication of the counter the extinction or absorbance $E_A$ is immediately available due to its logarithmic proportion to the time.

Other advantages are obtained by utilizing a step switch to provide variable resistance in parallel with the capacitor which is charged by the voltage proportional to the comparison light beam. One can thereby control the slope of the discharge curve and the time constant of the capacitor discharge period. A constant factor F can thus be adjusted which can serve to determine the concentration, i.e. a direct indication of concentration.

In another inventive aspect, the capacitor is about 10% overcharged. This advances the commencement of the discharge of the capacitor, i.e. the null point of the photometer. Advancement of the null point serves to obtain approximately similar proportions for the commencement and cessation of the discharge curve. Further, to this arrangement it is possible to alter the commencement of capacitor discharge which is also advantageous in controlling the null point.

The employment of comparators is also advantageous in the invention. These comparators compare the voltage of the test and comparison cells and provide a voltage proportional signal which is employed for the forming of time impulse $t$. The result is a simplified construction of the apparatus.

The partially transparent mirror used in the photometer of the present invention is employed in connection with an analog amplifier for important and unique advantages. The mirror needs to split only a signal of proportionally small intensity, which signal is then further amplified with an analog amplifier so that it corresponds to the intensity of the light beam applied to the cuvette. The major portion of the light of the light source is applied to the test sample to generate the light emerging from the test sample.

In a known way, through a backing device, a comparison light beam will be split before the cuvette with the test sample. The comparison light beam illuminates a photoelectric cell to provide a voltage which is amplified proportional to the intensity of the light beam applied to the cuvette. The test sample in the cuvette is illuminated and the intensity thereof related to the intensity of the comparison light beam. The light emerging from the cuvette does not contain the portion absorbed in the test sample. A voltage produced by the emerging light is led to an amplifier in a manner similar to that produced by the comparison light beam.

BRIEF DESCRIPTION OF THE DRAWINGS

FIG. 1 is a simplified schematic diagram showing the generation of the light beams, the analog amplifiers, and the analysis circuitry.

FIG. 3 is a simplified schematic diagram of circuitry for the evaluation of the two light rays with quotient forming for providing a voltage impulse to control a digital counter.

DESCRIPTION OF THE PREFERRED EMBODIMENT

Figure 2A:
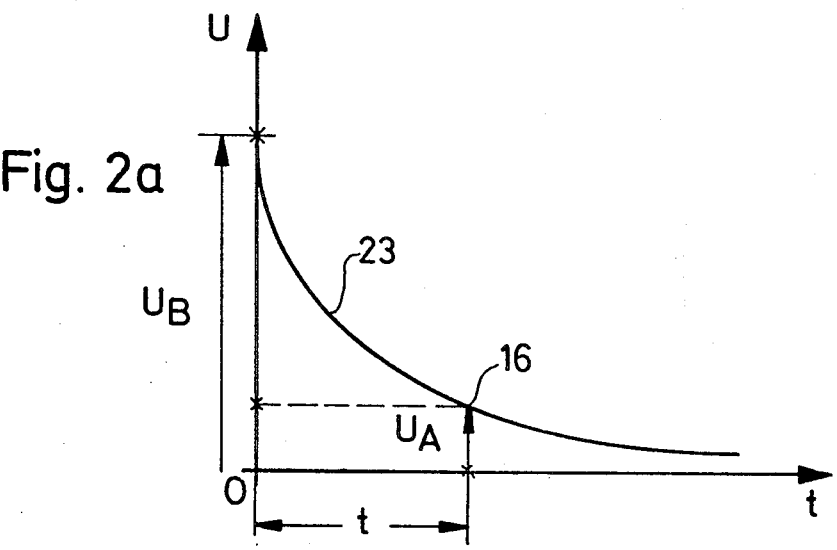
FIG. 2a shows the discharge curve of a condenser and the voltage magnitudes corresponding to the comparison and measure light beams.

Turning now to FIG. 1, light source 1, which may, for example, be a mercury lamp, provides a beam of light. The light passes through filter 2 and strikes partially transparent mirror 7. A sizable portion of the light passes through mirror 2. This portion is applied to cuvette 3 containing the fluid samples to be analyzed. The fluid partially absorbs the light, providing an indication of its properties, and the emerging light from the cuvette is received by photoelectric cell 4 coupled to analog amplifier 5. The output signal is conductor 6 of amplifier 5, which is subjected to electronic analysis, may hereinafter be termed Signal A.

The reflected beam 8 of mirror 7 is of lesser intensity and serves as a comparison signal. The reflected or comparison light beam 8 is received by comparison photoelectric cell 9 and provided to analog comparison amplifier 10. Amplifier the signal resulting from comparison light beam 8 to the point where it corresponds to the intensity of the light beam applied to cuvette 3. The amplified signal in conductor 11 may be hereinafter called Signal B. Both Signal A and Signal B are applied to electrical analysis circuitry 12. Circuitry 12 will form the time t corresponding to the logarithm of the two signals A and B [$t = \log(B/A)$].

Mirror 7 is provided with a thin reflective coating, advantageously to provide a small portion of the light beam from light source 1 as comparison ray 8 to controlled amplifier 10. The major portion of the light beam of light source 1 is passed through cuvette 3 because comparison beam 8 used to obtain signal B corresponding to the light beam applied to cuvette 3, may be amplified to the desired level by amplifier 10.

In FIG. 2a, the form of the value $t = \text{Log.}(B/A)$ is shown by discharge characteristic of a capacitor. FIG. 3 shows capacitor 13, which for purposes of enhancing precision may be formed out of may small parallel capacitors, will be charged by transistor 14 with the signal in conductor 11. As noted above, the signal in conductor 11 is signal B which is proportional to the intensity of the light beam applied to cuvette 3. Voltage to which capacitor 13 is charged may be identified in FIG. 2a as voltage $U_B$. In parallel with capacitor 13 is a variable resistance 15, hereinafter described, for discharging capacitor 13 after each charging along a known exponential discharge curve.

Discharge time t of capacitor 13 will terminate when stop point 16 of the declining discharge curve 23 is reached. Point 16 corresponds to voltage $U_A$ which is proportional to the intensity of the light beam emerging from the test sample in cuvette 3. Time t is thus the time which elapsed as the voltage on condenser 13 sinks from the charging voltage $U_B$ to the voltage $U_A$. The exponential discharge curve produces the relationship $t = \text{Log.}(B/A)$ proportional to $E_A$ where $E_A$ is directly the absorbance or extinction E of the analysis.

Variable resistor 15 connected in parallel with capacitor 13 can, by means of switch 28, control the steepness of the exponential curve and specifically the time constant of the discharge. One can therewith adjust a factor F which serves to determine the concentration of the analysis and which makes it possible to directly show this concentration. When the factor F is one the discharge time $t$ is proportional to the extinction coefficient $E_A$. The factor F may be chosen so that the discharge time t is proportional to the concentration $C = E_A \times F = F \times \text{Log.}(B/A)$.

The apparatus is particularly favorable for digital indication because the result appears proportional to a time and not in the form of a voltage. Thus, for example, will a digital indicator 27 of counter 26 be controlled by generator 20 with a constant frequency through a gate 19. The gate will be opened by the leading edge 29 of the time impulse $t$ and closed by the trailing edge 30 of the time impulses $t$. During the time $t$ the counter runs and shows directly the extinction $E_A$ and, by the factor F the concentration C.

Figure 2B:
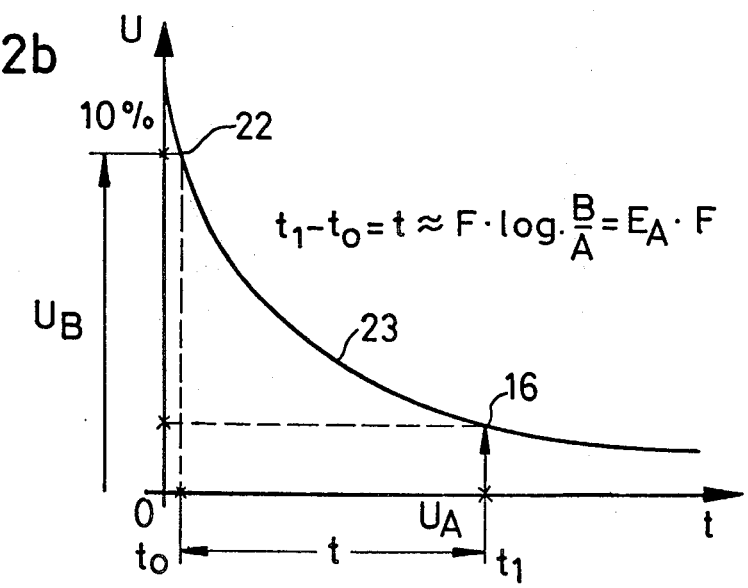
FIG. 2b shows a discharge curve, similar to FIG. 2a with a displacement of the null point.

In FIG. 2b is shown a quotient development similar to FIG. 2a however with a displaced null point $t_o$. For this purpose capacitor 13 is about 10% overcharged. The operation of the counter now begins at time $t_o$. Through this technique, clearly defined start and stop point 22, 16 of the discharge curve 23 of condensor 13 are obtained. It is also possible to effect adjustment in the small negative time range between 0 and $t_o$ in order to control the constant of null point $t_o$.

With this method of quotient forming by an exponential discharge curve, one obtains, as well as result in the form of a time t which is directly proportional to the desired result. There is an additional great advantage that the result is independent of the brightness of light source 1 that is, the brightness deviations of the light source, since through the quotient formation, these errors mutually compensate. Not only is the operation more simple, but the burning time of light source 1 is shorter because deviations in light intensity (flicker) are not included in the result. The test procedure can begin in approximately five minutes. Not only is the measurement procedure independent of variations in light intensity, it is also independent of the brightness of the lamp.

FIG. 3 is a schematic of analytical circuitry in simplified form.

The voltage in conductor 11, that is, Signal B (of FIG. 1) and corresponding to comparison light beam 8 is applied to comparator 17 in conductor 31. The voltage in conductor 11 corresponding to Signal B is also applied to amplifier 10a which increases the magnitude of the signal by 10%. The output of amplifier 10a is applied to switching transistor 14. Transistor 14 is periodically rendered conductive by a signal applied to its base to provide the increased output signal of amplifier 10a at the input 24 of circuitry 12 to charge capacitor 13. As noted previously, adjustable resistor 15 and step switch 28 may establish a factor which will adjust the operation of capacitor 13 to provide an indication of a concentration C of the analysis. At the same time the voltage in conductor 6, comprising Signal A of FIG. 1 and corresponding to the intensity of the light beam emerging from cuvette 3 is applied to the other input terminal 25 of analysis circuitry 12.

The comparison of the voltage Signal B in conductor 31 and the capacitor voltage in conductor 32 operates comparator 17 to start the counting process by means of gates 18 and 19, whereby the frequency of generator 20 is applied to counting elements 26. The counting process begins in FIG. 2b at the time $t_o$ that is, as soon as capacitor 13 reaches the voltage $U_B$ after being approximately 10% overcharged by the signal from amplifier 10a and switching transistor 14. Subsequently the capacitor begins to discharge across adjustable resistor 15 along the discharge curve 23.

The comparison of voltage Signal A in conductor 33 and the capacitor voltage in conductors 32 and 34 operates comparator 21. Specifically when the capacitor voltage reaches the voltages $U_A$, as a time $t_1$ in FIG. 2b comparator 21 which continuously compares the voltage $U_A$ and the capacitor voltage is deenergized to close gates 18 and 19 and stop the counting process. The indicator of the counter provides a result directly in the form of a concentration $C = E_A = F$ proportional $t = t_1 - t_o$.

Through the comparison intensity of the comparison light beam, i.e. the voltage $U_B$, which corresponds to the intensity of the light applied to the cuvette, and the intensity of the emerging light beam from the cuvette, i.e. voltage $U_A$, a time impulse will be formed which, through the quotient formation process will be independent of the light variations of the light source and which provides a proportional readout result. Through the construction of the apparatus with integral switching and a five step illuminated digital indicator will be highest demand of exactness in test results be met. If desired, a highest order of readout device may be utilized to exclude errors. The provision of each calibration curve as well as the calculation of the end result on the basis of determined extinction values can be accomplished easily.

In spite of the use of a mercury lamp, the apparatus is prepared for absolutely constant results in five minutes. This is possible because the mercury lamp light beam is separated into the measuring and comparison light beams for application to two different photocells. The variation of the mercury lamp (flicker) through the foregoing arrangement is compensated.

Various modes of carrying out the invention are contemplated as being within the scope of the following claims particularly pointing out and distinctly claiming the subject matter which is regarded as the invention.

We claim:

1. A photometer for providing an indication of the light absorption properties of a test sample comprising:

test signal means (4, 5) for providing a first voltage proportional to the intensity of a light beam emerging from the test sample (3);

comparison signal means (9, 10) for providing a second voltage proportional to the intensity of a light beam applied to the test sample;

capacitor means including a capacitor (13), amplification means (10a) coupled to said comparison signal means (9, 10) and to said capacitor (13) for amplifying said second voltage by a predetermined amount and for applying same to said capacitor to charge said capacitor to a voltage in excess of said second voltage, said capacitor means including first sensing means (17) coupled to said capacitor (3) and said comparison signal means (9, 10) for initiating a discharge time period when said capacitor discharges to said second voltage, said capacitor means further including second sensing means (21) coupled to said capacitor (13) and said test signal means (4, 5) for sensing when said capacitor has further discharged to said first voltage for terminating said time period; and means (26) coupled to said capacitor means (13) for providing the discharge time period of the capacitor as an indication of the light absorbing properties of the test sample.

2. The photometer of claim 1 wherein said first sensing means includes first comparator means coupled to said capacitor and to said comparison signal means and said second sensing means includes second comparator means coupled to said capacitor and to said test signal means.

3. The photometer of claim 1 wherein said capacitor means includes means for altering the discharge characteristic and time period of the compacitor.

4. The photometer of claim 3 including variable resistance means coupled to said capacitor for altering the discharge characteristic and time period thereof.

5. The photometer of claim 1 including a light beam source and means for providing said emerging light beam and said applied light beam from said light beam source.

6. The photometer of claim 5 including means for splitting a low intensity beam portion from the light beam source and providing an electrical signal proportional thereto and means for amplifying said signal for providing said second voltage.

7. The photometer of claim 1 wherein said indicator means includes a coincidence gating means having an output coupled to a digital counter and inputs coupled to said capacitor means and a frequency generator for providing output pulses of said frequency generator to said digital counter during said time period as said indication.

* * * * *